United States Patent [19]
Kocher, Jr.

[11] Patent Number: 5,743,272
[45] Date of Patent: Apr. 28, 1998

[54] MALE NIPPLE ABRASION PROTECTOR

[76] Inventor: Robert W. Kocher, Jr., 4828 N. 3rd St., Arlington, Va. 22203

[21] Appl. No.: 629,867

[22] Filed: Apr. 10, 1996

[51] Int. Cl.$^6$ ............................................. A61F 5/37
[52] U.S. Cl. .................................. 128/846; 128/890
[58] Field of Search ............................ 128/846, 889, 128/890; 602/41

[56] References Cited

U.S. PATENT DOCUMENTS

| | | | |
|---|---|---|---|
| 16,396 | 1/1857 | Parker | 128/890 |
| 1,165,275 | 12/1915 | Montgomery | 128/890 |
| 4,333,471 | 6/1982 | Nakai | 128/890 |
| 5,171,321 | 12/1992 | Davis | 128/890 |

*Primary Examiner*—Michael A. Brown

[57] ABSTRACT

A common problem among male distance runners and athletes is male nipple abrasion from tee shirts or jerseys during extended exercise. Some men suffer severe chafing and bleeding nipples when they run long distances caused, in large part, as salt crystals forming as perspiration evaporates. The Male Nipple Abrasion Protector device is formed to fit comfortably over the nipple with an adhesive backing that adheres to the dark nipple area (base). The external material has low friction allowing to easily slide against a tee shirt, sweat shirt, normal shirt or outer wear. The adhesive backing will resist perspiration and can be easily removed when desired. The protectors are simple, low cost and disposable. The Male Nipple Abrasion Protector does not require straps or bra type configurations.

4 Claims, 2 Drawing Sheets

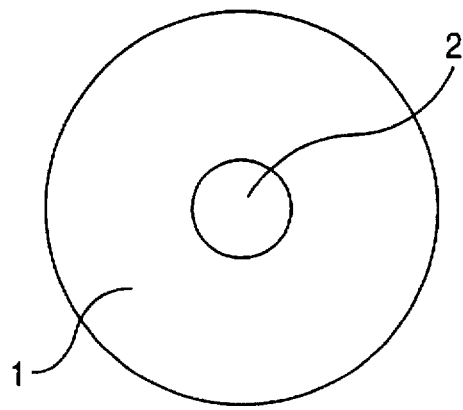
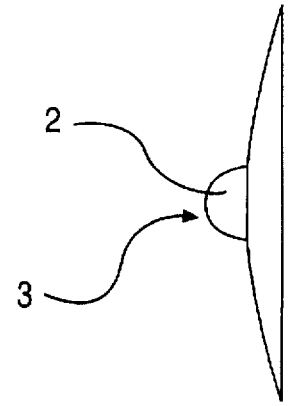
FIG. 1  FIG. 2
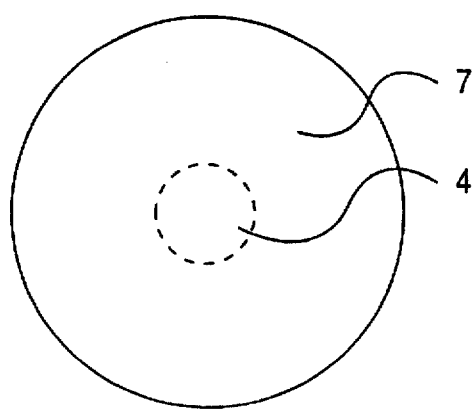
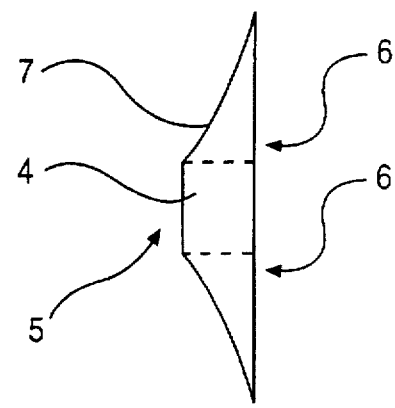
FIG. 3  FIG. 4

MALE NIPPLE ABRASION PROTECTOR

CROSS-REFERENCE TO RELATED APPLICATIONS

None listed.

BACKGROUND OF INVENTION

1. Field of Invention

This invention primarily pertains to males engaged in physical activities but also has substantial application to men wearing shirts without undershirts. This invention can also be applied to any male (or in some cases females) that has nipple abrasion problems. Common nipple abrasion problem exists among male runners jogging extended distance and male athletes. This problem is the result of friction from a simple tee or sweat shirt rubbing over chest nipples. Most male distance runners have this problem and commonly causes painful abrasions resulting in bleeding. This painful condition may exist for several days until properly healed. A marathon runner may take 25,000 steps to cover the 26.2 miles. Each step causing friction on the runner's nipple no matter how soft a tee shirt may feel. In the book, *Making the Marathon Your Event* by Richard Benyo, he writes: "Some men have a tendency to suffer bleeding nipples when they run long distances—this is caused, in large part, as salt crystals forming as perspiration evaporates. The salt crystals eventually build up to cause severe chafing."

2. Closest Known Prior Art

Currently most runners will engage in a messy, unreliable approach of smearing a large glob of petroleum jelly over the nipples and/or cover with a long strip of tape. The tape commonly comes loose and the jelly tends to rub off the nipple. If the tape holds, it is difficult to take off afterwards due to its required length and its adhesion to chest hairs. The taping does not conform to the nipple and is uncomfortable on the chest. Males not engaged in athletic activity are normally protected by tee-shirts from the rubbings of a normal shirt. Bras could be used but this requires straps or bands and normally males are not in favor of wearing bras. Weather permitting, many runners will run without a shirt to avoid abrasion.

BRIEF DESCRIPTION OF THE DRAWINGS

FIG. 1 is a front vies of the device.

FIG. 2 is a side view of a normal male nipple.

FIG. 3 is a front view of the protector.

FIG. 4 is a side view of the protector.

DESCRIPTION OF DRAWINGS

The drawings, FIG. 1 is a front view and FIG. 2 is a side view (larger than actual size) of a nominal male nipple. Item 1 is the nipple base, that is, the brown area with no hair. This is the primary surface to which the protector is attached. Item 2 is the nipple itself and item 3 is the tip of the nipple on which painful abrasion occurs. FIG. 3 is a front view drawing of the protector and FIG. 4 is a side view. The shape of front and side views can vary and the sizes will also vary to accommodate various size nipples i.e. small, medium, large and extra-large. The general configuration need not be circular since the majority of motion appears to be in the up and down direction. Circular configurations can contribute to ease in putting on since orientation would not be necessary. Item 4 is a hollow area with no adhesive in which the nipple tip is inserted. Item 5 is a cover of the nipple tip. Item 6 is the adhesive surface area that attaches to the brown nipple area, Item 1. Material configurations can vary to reduce cost and weight. Materials configurations can also optimize comfort, protection and minimize friction against material surface. Item 7 is the base of the protector.

The Male Nipple Abrasion Protector is an inexpensive nipple protector for use on a human body to minimize abrasion on the nipple surface. The device consists of a base portion sized to contact and cover a portion of the area surrounding the nipple to be protected: a base portion having an aperture formed thereby allowing the nipple to protrude there through without irritation; a cover attached to the base portion that is disposed over and encloses the aperture and an adhesive layer disposed on the side of the base member opposite the cover and being suitable for attaching and holding the nipple protector in place during exercise when exposed to normal body secretions caused during exercise.

Figure 5:
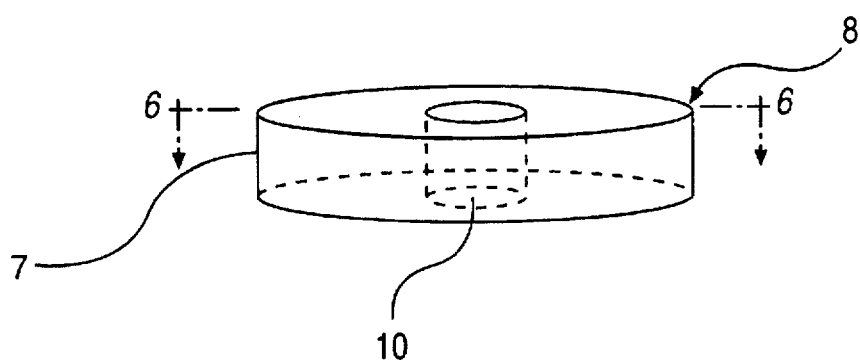
FIG. 5 is a side view of the protector.
Figure 6:
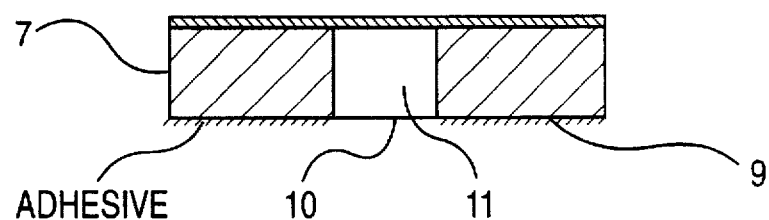
FIG. 6 is a side view of the protector.
Figure 7:
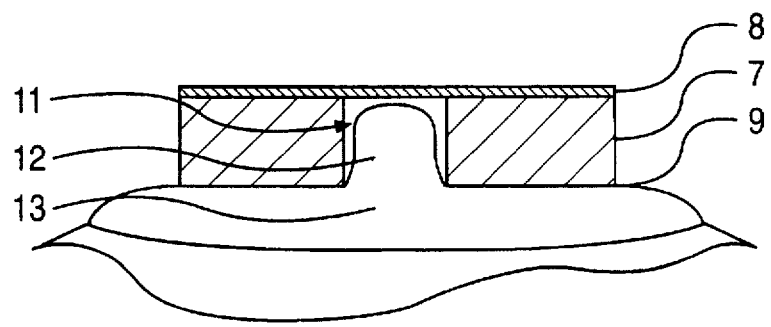
FIG. 7 is a side view showing the protector attached to the male nipple.

FIGS. 5,6 and 7 show a disk version of the Male Nipple Abrasion Protector. The device's body (Item 7), material cover (item 8) with an adhesive backing (Item 9) adhere to a nipple base. The Protector's bottom has an aperture (Item 10) to allow the nipple to pass into the protector's cavity (Item 11). The nipple is protected from abrasion by the cavity walls and the cover (Item 8).

FIG. 7 shows a drawing of the nipple protector in place on a male nipple. Item 12 is the nipple and Item 13 is the male nipple base. The nipple rests comfortably in the protector's cavity (Item 11). The protector is held on by an adhesive layer (Item 9) and the nipple is protected in the cavity (Item 11) by the device's body (Item 7) and cover (Item 8).

Packaging the nipple protectors can be accomplished individually by covering the adhesive surface (Item 9) with a peel-off wax paper type of material or placing several protectors on a treated paper sheet allowing the protectors to be distributed in small sheets and peeled off when needed.

I claim:

1. An inexpensive nipple protector for use on a human body to minimize abrasion on the nipple surface including: a base portion sized to contact and cover a portion of the area surrounding the nipple to be protected, the base portion having an aperture formed therein the aperture allowing the nipple to protrude there through without irritation, a cover attached to the base portion that is disposed over and encloses the aperture forming a cavity and an adhesive layer disposed on the side of the base member opposite the cover and being suitable for attaching and holding the nipple protector in place during exercise when exposed to normal body secretions caused during exercise.

2. A nipple protector of claim 1 wherein the device's basic structure is a thick disk with said aperture for the nipple to enter the cavity and a cover to protect the nipple tip.

3. A nipple protector of claim 1 wherein the device's basic structure is thick enough to exceed the length of the nipple and no cover or enclosure is required on the nipples' end.

4. A nipple protector of claim 1 of various sizes and shapes.

* * * * *